United States Patent
Messano, Jr. et al.

(10) Patent No.: US 8,971,998 B2
(45) Date of Patent: *Mar. 3, 2015

(54) SYSTEMS AND METHODS FOR MULTISPECTRAL SCANNING AND DETECTION FOR MEDICAL DIAGNOSIS

(71) Applicants: Albert Francis Messano, Jr., Montvale, NJ (US); Mandeep Singh, Lodi, NJ (US)

(72) Inventors: Albert Francis Messano, Jr., Montvale, NJ (US); Mandeep Singh, Lodi, NJ (US)

(73) Assignee: Integral ElectroMagnetronic Technologies LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/835,268

(22) Filed: Mar. 15, 2013

(65) Prior Publication Data

US 2013/0218021 A1     Aug. 22, 2013

Related U.S. Application Data

(63) Continuation-in-part of application No. 12/957,584, filed on Dec. 1, 2010.

(60) Provisional application No. 61/282,218, filed on Dec. 31, 2009.

(51) Int. Cl.
*A61B 5/00*     (2006.01)
*A61B 5/01*     (2006.01)

(52) U.S. Cl.
CPC ............. *A61B 5/0062* (2013.01); *A61B 5/0093* (2013.01); *A61B 5/015* (2013.01)
USPC ........................... 600/473; 600/474; 600/475

(58) Field of Classification Search
USPC ................................. 600/473–475
See application file for complete search history.

(56) References Cited

U.S. PATENT DOCUMENTS

| | | | |
|---|---|---|---|
| 4,148,005 A | 4/1979 | Larsen et al. | 338/28 |
| 5,912,179 A | 6/1999 | Alvarez et al. | 436/63 |
| 7,167,742 B2 | 1/2007 | Camacho et al. | 600/473 |
| 8,041,414 B2 | 10/2011 | Peter et al. | 600/427 |
| 2003/0093092 A1 | 5/2003 | West et al. | |

(Continued)

OTHER PUBLICATIONS

FCC Public Notice. "FCC Releases Revised Bulletin on Compliance with New Guidelines for Exposure to Radiofrequency Electromagnetic Fields". Aug. 25, 1997. Retrieved Jan. 8, 2014 from <http://transition.fcc.gov/Bureaus/Engineering_Technology/Public_Notices/1997/pnet7018.html>.

(Continued)

*Primary Examiner* — Long V Le
*Assistant Examiner* — Colin T Sakamoto
(74) *Attorney, Agent, or Firm* — Greenberg Traurig, LLP

(57) ABSTRACT

The present invention relates to systems and methods for detecting biomaterial anomalies in a test subject for diagnosing existing and potential medical conditions. The general technique utilized is to expose a portion of the test subject to low doses of RF electromagnetic energy. Different biomaterials in a test subject may be differentiated and identified by characterizing their electromagnetic properties based on observed parameters, e.g., electromagnetic energy absorbed, thermal energy created, and electromagnetic energy emitted, during irradiation of the test subject. This invention allows for the efficient utilization of multiple frequency bands allowed by the FCC, as well as a more precise distribution of electromagnetic energy to the test subject.

20 Claims, 2 Drawing Sheets

(56) References Cited

U.S. PATENT DOCUMENTS

Figure 1:
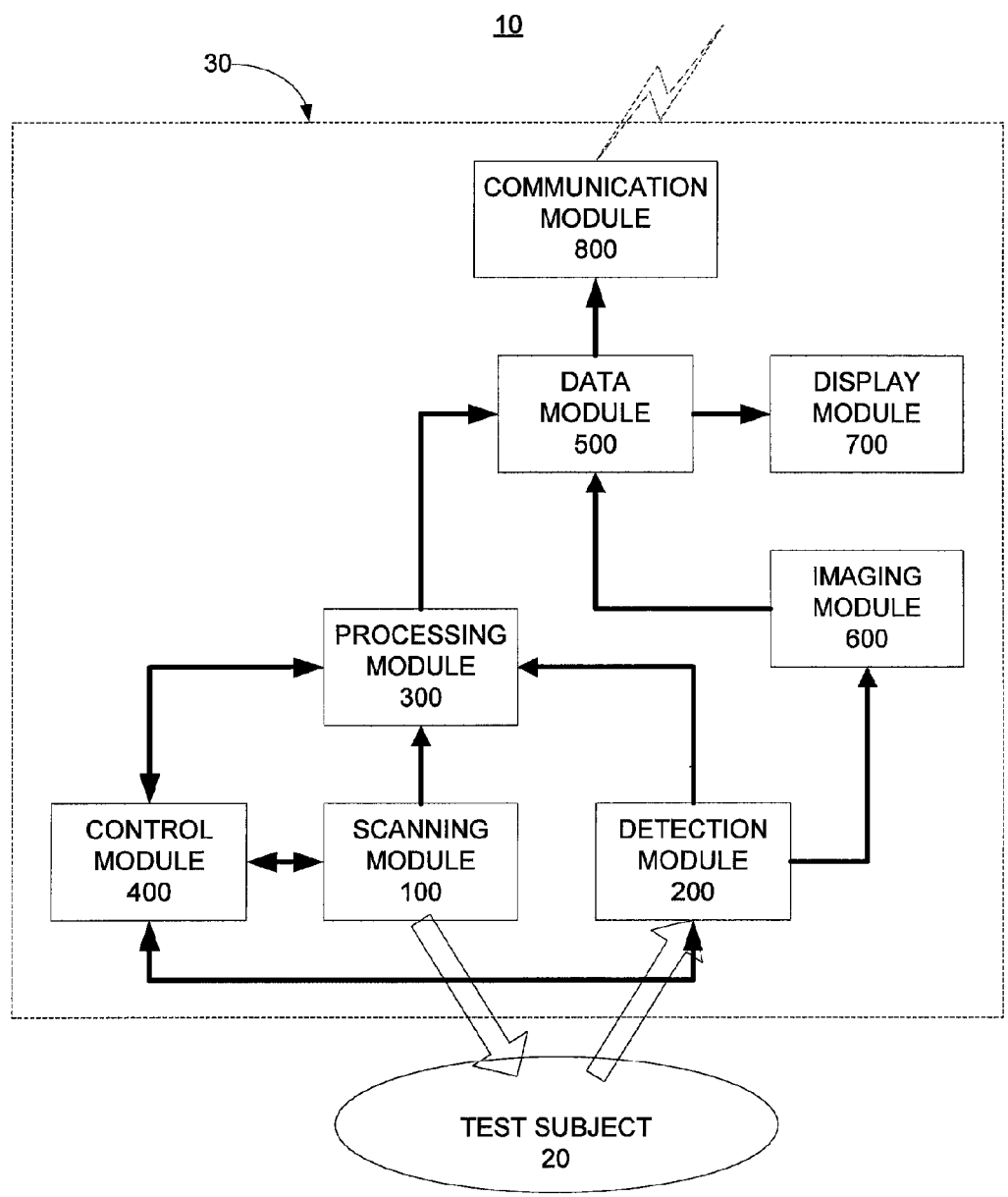

| | | | |
|---|---|---|---|
| 2004/0186383 A1 | 9/2004 | Rava et al. | 600/473 |
| 2005/0020924 A1 | 1/2005 | Mitra | 600/474 |
| 2006/0089556 A1 | 4/2006 | Bambot et al. | 600/476 |
| 2007/0093708 A1 | 4/2007 | Benaron et al. | 600/407 |
| 2007/0112273 A1 | 5/2007 | Rogers | 600/475 |
| 2007/0167782 A1 | 7/2007 | Callahan et al. | |
| 2007/0189359 A1 | 8/2007 | Chen et al. | |
| 2007/0287913 A1 | 12/2007 | Regni | 600/439 |
| 2008/0123083 A1 | 5/2008 | Wang et al. | 600/437 |
| 2008/0161674 A1 | 7/2008 | Monro | 600/410 |
| 2008/0269616 A1 | 10/2008 | Bloom et al. | 600/475 |
| 2009/0105588 A1 | 4/2009 | Emelianov et al. | |
| 2009/0213617 A1 | 8/2009 | Sander | 362/575 |
| 2009/0292211 A1 | 11/2009 | Lin et al. | 600/476 |
| 2009/0326383 A1 | 12/2009 | Barnes et al. | 600/476 |
| 2010/0041998 A1 | 2/2010 | Postel | 600/475 |
| 2010/0113861 A1 | 5/2010 | Biris et al. | |
| 2010/0139946 A1 | 6/2010 | Schmidt et al. | |

OTHER PUBLICATIONS

Brauer. Safety and Health for Engineers, Second Edition. @ 2006, John Wiley & Sons, Inc. Chapter 21, 383-398.

Microtrans, "Some aspects on the microwave penetration depths and dielectric properties of foods" (1999).

Ybarra et al., "Microwave Breast Imaging," Chapter 16, Emerging Technology in Breast Imaging and Mammography, American Scientific Publishers, pp. 1-12 (2007).

US Appl. No. 12/957,584, Non-Final Office Action, Jul. 27, 2012.

US Appl. No. 12/957,584, Final Office Action, Dec. 5, 2012.

US Appl. No. 12/957,584, Non-Final Office Action, Apr. 10, 2013.

US Appl. No. 12/957,584, Non-Final Office Action, Aug. 30, 2013.

Arabi et al., "Breast Carcinoma Detection at early stage by FIR radiation of Microwave heated Breast Tissues," Proceedings of the 2008 International Conference on Computing, Communications and Networking (ICCCN 2008). IEEE.

Cleveland et al., Evaluating Compliance with FCC Guidelines for Human Exposure to Radiofrequency Electromagnetic Fields. Federal Communications Commission, Office of Engineering & Technology (Aug. 1997).

Nowakowski, "Quantitative Active Dynamic Thermal IR-Imaging and Thermal Tomography in Medical Diagnostics," pp. 7-1 to 7-29. Medical Infrared Imaging, edited by Nicholas A. Diakides and Joseph D. Bronzino, Taylor & Francis Group (2008).

Pettersson et al., "Phantom," Encyclopaedia of Medical Imaging. Taylor & Francis, p. 303 (1999).

Poplack et al., "Electromagnetic Breast Imaging: Average Tissue Property Values in Women with Negative Clinical Findings," Radiology, 231(2):571-580, RSNA (2004).

Schaefer et al., "Adopting the DICOM standard for medical infrared images," Proceedings of the 28th IEEE EMBS Annual International Conference, New York City, USA (2006). IEEE.

ITU Radio Regulations, Article 2, Nomenclature, Section I—Frequency and Wavelength Bands. Updated Sep. 1, 2005.

Office Action issued in U.S. Appl. No. 13/564,054, filed Aug. 1, 2012.

SYSTEMS AND METHODS FOR MULTISPECTRAL SCANNING AND DETECTION FOR MEDICAL DIAGNOSIS

TECHNICAL FIELD

This invention relates to technology for detecting biomaterial anomalies in a test subject for diagnosing existing and potential medical conditions.

BACKGROUND

Existing biomedical imaging techniques such as MRI, CAT scans, ultrasonic scans, nuclear medicine, and X-ray all have limitations. These include, but are not limited to, exposure to high energy with potential for damage, ingestion of imaging agents, physical contact with the subject and confining environments. Thus, it would be beneficial to provide a biomedical imaging technique that obviates at least some of these limitations.

SUMMARY OF THE INVENTION

The present invention is directed to systems and methods for detecting biomaterial anomalies in a test subject for diagnosing existing and potential medical conditions. The general technique utilized is to expose a portion of the test subject to low doses of RF electromagnetic energy. Different biomaterials in a test subject may be differentiated and identified by characterizing their electromagnetic properties based on observed parameters, e.g. electromagnetic energy absorbed, thermal energy created, and electromagnetic energy emitted, during irradiation of the test subject.

In accordance with one aspect of the invention, provided is a system for multispectral scanning and detecting biomaterials in a test subject. In one embodiment, the system may comprise a scanning module, a detection module, and an imaging module. The scanning module is preferably adapted to deliver electromagnetic energy to the test subject by radiation at selected frequencies, duty cycle and power. The detection module is preferably adapted to detect RF electromagnetic radiation reflected by test subject and IR electromagnetic radiation emitted by the test subject. The imaging module is preferably adapted to process, condition, and format data collected by the detection module and to communicate this data to produce a thermal image of the test subject.

In another embodiment, the system may further comprise a processing module, a control module, and a data module. The processing module is preferably connected to the scanning and detecting modules so that it can perform calculations for the control and data modules. The control module is preferably connected to the scanning module, detection module, and processing module in order to control the timing, power level, antenna gain, and scan frequency of the scanning module. The data module preferably processes data from the processing module and the imaging module and structures the data into video format. In another embodiment, the imaging data may be made available to both a local operator through a display module and to a remote operator through a communication module.

In accordance with another aspect of the invention, provided are methods for multispectral scanning and detection of biomaterials in a test subject 20. In one implementation, a method for multispectral scanning and detection of biomaterials comprises irradiating the test subject with RF electromagnetic radiation, detecting IR electromagnetic radiation emitted by the test subject, and providing an image of the test subject differentiating different biomaterials.

In another implementation, the method of scanning and detection may further comprise measuring and/or calculating parameters of the RF electromagnetic radiation impinged on the test subject and adjusting irradiation of the test subject to comply with applicable FCC MPE limits while maximizing the depth of penetration to ensure proper scanning of the test subject.

In another implementation, the method of scanning and detection may further comprise measuring and/or calculating parameters of the test subject during irradiation; calculating electromagnetic properties of biomaterials in the test subject based on the measured and/or calculated parameters of the test subject during irradiation; and differentiating and/or identifying biomaterials in the test subject based on the electromagnetic properties of different biomaterials.

These and other aspects of the invention will become apparent from the present specification and claims.

BRIEF DESCRIPTION OF THE DRAWING FIGURES

Figure 2:
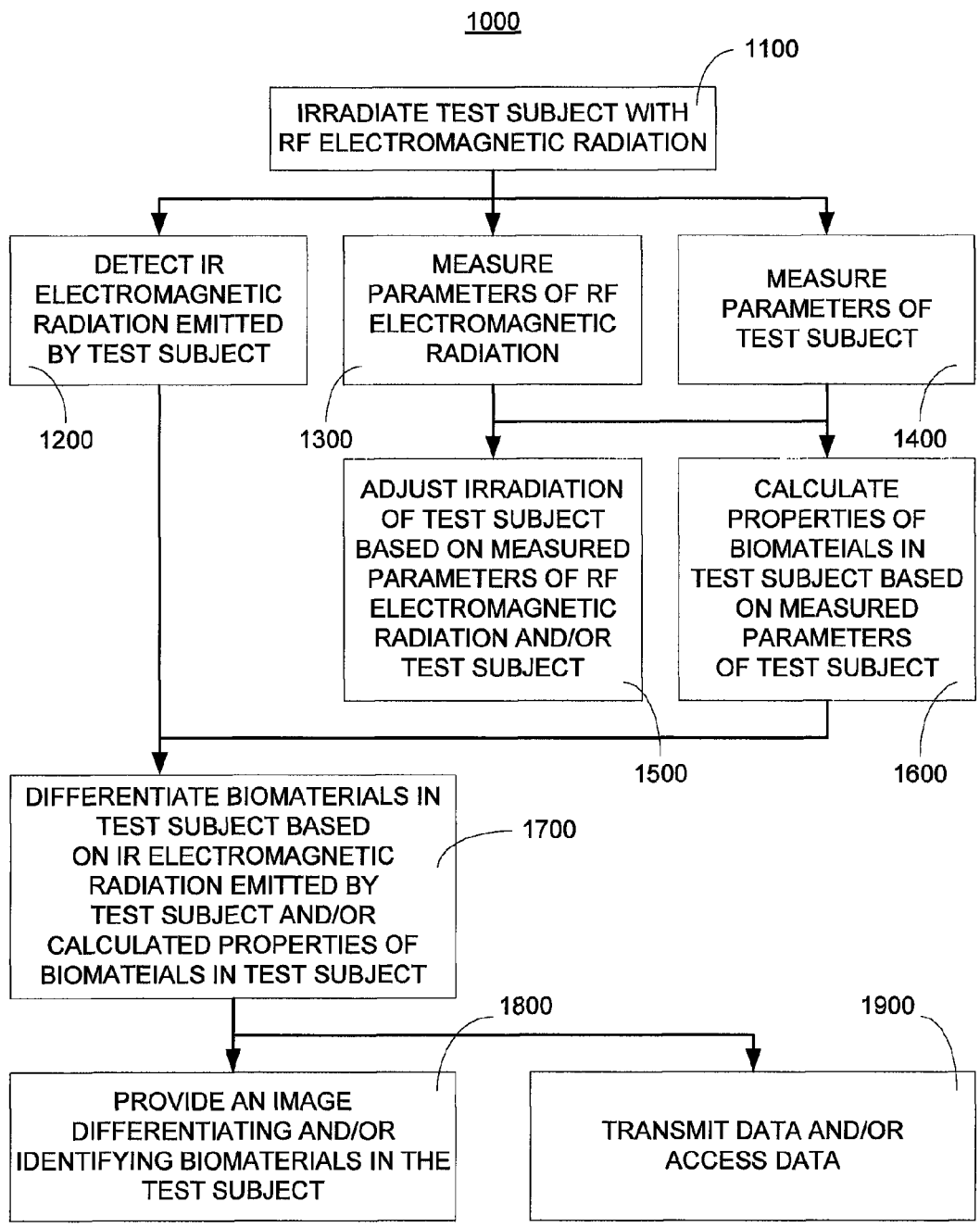

FIG. 1 is a schematic illustration of an exemplary system for multispectral scanning and detecting biomaterials in a test subject; and FIG. 2 is a flowchart of an exemplary implementation of a method for multispectral scanning and detecting biomaterials in a test subject.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

This invention relates to technology for detecting biomaterial anomalies in a test subject for diagnosing existing and potential medical conditions. The general technique utilized is to expose a portion of the test subject to low doses of RF electromagnetic energy. Some of the RF electromagnetic energy radiated to the test subject is absorbed by the test subject and converted into thermal energy. The test subject is comprised of different biomaterials having different electromagnetic properties, and therefore, electromagnetic energy is absorbed differentially by different biomaterials. As a result, different biomaterials in the test subject produce thermal energy at different rates. Further, some of the thermal energy produced by the test subject is radiated as IR electromagnetic radiation, which is also emitted differentially by different biomaterials depending on their electromagnetic properties.

The electromagnetic properties of the biomaterials comprising the test subject determine how much RF electromagnetic energy is absorbed, converted into thermal energy, and emitted as IR electromagnetic energy. Thus, different biomaterials may be differentiated and identified by characterizing their electromagnetic properties based on observed parameters of the biomaterials (e.g. electromagnetic energy absorbed, thermal energy created, and electromagnetic energy emitted).

System

In accordance with one aspect of the invention, provided is system 10 for scanning and detecting biomaterials in test subject 20. In one embodiment as shown in FIG. 1, system 10 may comprise scanning module 100, detection module 200, processing module 300, control module 400, data module 500, imaging module 600, display module 700, and communication module 800. In the embodiment shown, system 10 is organized into separate modules, but one skilled in the art will appreciate that one of these modules or portions thereof may be combined with another of these modules or portions thereof. The various modules of system 10 are described in further detail below. The headings provided herein are for convenience only and do not interpret the scope or meaning of the claimed invention.

Preferably, system 10 is contained in a portable, hermetically sealed and robust package 30 of military standard construction with a footprint of approximately 14"×10" so that system 10 may be easily deployed in field applications. Further, system 10 is preferably packaged in a unit of roughly the same size and weight as a small laptop-sized device. The display is expected to be approximately 14" diagonal. The resolution of images is expected to be approximately 2048× 1536 pixels using an OLED screen. Controls will be sealed soft-keys and embedded cursor. This means that the imager will be robust enough for extreme environmental conditions. Use of commercial-off-the-shelf components will insure high quality and performance, yet low materials cost. It is anticipated that a rechargeable lithium-polymer battery will be the power source. All external enclosure connectors and penetrations will be military standard. Imaging data will be transmitted via WiFi, satellite or commercial wireless carriers with appropriate encryption to safeguard sensitive patient information.

Scanning Module

Scanning module 100 is adapted to deliver electromagnetic energy to test subject 20 by radiation at selected frequencies and power. Preferably, the electromagnetic energy is radiated to test subject 20 is in the radio frequency range of the electromagnetic spectrum. In one embodiment, scanning module 100 comprises a signal generator coupled to an antenna that amplifies and transmits electromagnetic energy to test subject 20 over an RF path. As such, scanning module 100 is subject to Federal Communications Commission (FCC) regulation. The FCC establishes guidelines for operations and devices to comply with limits for human exposure to radiofrequency (RF) fields adopted by the FCC and publishes these guidelines in OET Bulletin 65. According to FCC guidelines, the limits of Maximum Permitted Exposure (MPE) to electromagnetic radiation with frequencies of 0.3 MHz-100,000 MHz depend on frequency and are listed in Table 1.

Preferably, the signal generator has a variable power output of 1 mW-1000 mW and a duty cycle of 100% or less. Further, the signal generator is preferably adapted to produce non-ionizing electromagnetic radiation having frequencies with within FCC designated Industrial Scientific and Medical (ISM) bands. The frequency bands selected are designated as the 2.45 GHz, 5.8 GHz and 24.125 GHz bands. The respective frequency ranges are: 2.4-2.5 GHz, 5.725-5.875 GHz and 24-24.25 GHz. The antenna is designed to bathe test subject 20 with RF electromagnetic radiation from the signal generator. Preferably, the antenna is adapted to amplify the signal power of the electromagnetic radiation produced by the signal source with a variable Gain (G) of 1 dB-20 dB. Thus, the net amplified power output ($R_t$) from scanning module 100 depends on the output power ($P_t$) of the signal generator as well as the gain (G) of the antenna. This net amplified power output ($R_t$) may be described many ways, including Effective Isotropic Irradiated Power (EIRP) and Effective Radiated Power (ERP). For purposes of this discussion, net amplified power output ($R_t$) will be referred to as the EIRP, which is calculated as follows:

$$EIRP = G * P_t$$

As shown by the above equation, the EIRP of scanning module 100 may be controlled by adjusting the gain of the antenna and/or the power output of the signal generator.

Further, in another embodiment, scanning module 100 may also comprise a sonic proximity detector that is adapted to sense the length of the RF path, i.e., the distance that the electromagnetic radiation travels from the antenna to test subject 20.

The electromagnetic radiation delivered by scanning module 100 is subject to attenuation or energy loss due to the distance traveled from the antenna to test subject 20. This attenuation is a function of the distance from the antenna to test subject 20, the material between the antenna and test subject 20 (e.g. air), and the frequency of the electromagnetic radiation. Thus, in order to deliver the maximum allowable electromagnetic radiation while complying with applicable FCC limits of Maximum Permitted Exposure (MPE), the attenuation of electromagnetic radiation the 2.450 GHz, 5.8 GHz and 24.125 GHz bands must be monitored to ensure that the Power Density (S) is below the applicable FCC MPE limit. The amount of power transmitted to test subject 20 will vary as control module 400 adjusts scanning module's 100 output power $P_t$, antenna Gain G, and frequency to obtain maximum penetration of test subject 20 while complying with MPE limits.

Detection Module

Detection module 200 is adapted to detect RF electromagnetic radiation reflected by test subject 20 and IR electromagnetic radiation emitted by test subject 20 as absorbed RF electromagnetic radiation from the signal generator is converted into thermal energy by test subject 20. Detection module 200 scans test subject 20 being irradiated with RF electromagnetic energy and can detect the amount of RF electromagnetic energy reflected and the amount of IR electromagnetic energy emitted by test subject 20. When irradiated with RF electromagnetic energy of a given frequency, different biomaterials absorb and convert RF electromagnetic energy into thermal energy at different rates, and as a result, emit IR electromagnetic energy at different rates. Thus, by examining the RF electromagnetic energy reflected and the IR electromagnetic energy emitted by different portions of test subject 20, different biomaterials in a test subject 20 may be differentiated and identified. The data collected by detection module 200 may be processed, conditioned, and formatted by imaging module 600 to make a thermal image of test subject 20 available to both a local operator through display module 700 and to a remote operator through communication module 800. Further, the data collected by detection module 200 may be communicated to processing module 300 and data module 500 for differentiating and identifying the biomaterials of test subject 20.

Detection module 200 comprises an IR camera and detector. In one embodiment, the IR camera and detector preferably comprise a charge-coupled device (CCD) that senses IR electromagnetic radiation and produces analog electrical signals that are converted to digital signals for display as an image. Preferably, the CCD has a range of 1 μm to 200 μm wavelengths, which are considered Near IR (NIR) to Far IR (FIR). Detection module 200 preferably is sensitive to differential thermal heating of test subject 20 of 2° F. to 5° F. and differential thermal emission of test subject 20 of at least 3 mW/cm². Further, the CCD preferably has a nominal sensitivity of at least 0.1° K, a resolution of at least 2048×2048 pixels, and a data rate of at least 20 MHz and 50 MHz. Also, the CCD is preferably capable of at least a 16-bit analog-to-digital signal conversion.

Processing Module

Processing module 300 performs calculations that may be required by control 400 and data 500 modules. Preferably, processing module 300 comprises either a microprocessor (μP) or an application-specific integrated circuit (ASIC) configured to receive input signals from scanning 100 and/or detection 200 modules, perform calculations, and transmit output signals to control 400 and/or data 500 modules. Thus, in one embodiment, processing module 300 may be connected to scanning, and detecting modules so that it can receive operational data, perform calculations, and communicate signals/data to control 400 and data 500 modules.

In accordance with one aspect of processing module 300, processing module 300 receives operational data from scanning module 100 and performs calculations to determine different aspects of the system's 10 performance, such as EIRP, power density (S), power received ($P_r$), path loss, power incident, and power reflected.

For example, processing module 300 may perform calculations to determine whether system 10 is operating within the applicable FCC's MPE limits for power density. By receiving operational data from scanning module 100 regarding the gain, output power, and distance to test subject 20, processing module 300 may calculate the power density of the electromagnetic energy delivered to the test subject 20 and may send a corresponding signal control module 400, which can adjust operation of scanning module 100 to comply with the MPE limits for power density per the applicable FCC guidelines.

Thus, processing module 300 may be programmed to perform at least the calculations explained in detail below. For example, the net amplified power output, e.g., the Effective Isotropic Irradiated Power (EIRP), of scanning module 100 may be calculated using the equation:

$$EIRP = G * P_t,$$

where G is the antenna gain and $P_t$ is the power output of the signal generator. The antenna gain G and the power output $P_t$ are transmitted by scanning module 100 to processing module 300. Further, the power density (S), as defined by FCC OET 65, may be calculated using the equation:

$$S = EIRP/4\pi R^2,$$

where EIRP is the effective isotropic irradiated power of scanning module 100 and R is the distance between the antenna and test subject 20. The distance R is determined by scanning module's 100 proximity detector and transmitted to processing module 300. Thus, by receiving operational data from scanning module 100 regarding the gain G, power output $P_t$, and distance R, processing module 300 can determine whether scanning module 100 is operating within the FCC MPE limits for power density.

Processing module 300 will perform these calculations and provide control module 400 with a signal output corresponding to the power density (S) of system 10. Thus, control module 400 can compare the signal output corresponding to the power density (S) of system 10 to a reference value corresponding to the applicable FCC MPE limit for power density and adjust operation of scanning module 100 accordingly. Again, both the gain G and the power output Pt may be adjusted by control module 400 to maintain the applicable FCC MPE limit at the outer surface of the test subject 20 while maximizing power output and penetration depth.

Also, processing module 300 may be adapted to perform calculations to determine the actual power delivered to test subject 20, accounting for attenuation or power loss of the electromagnetic radiation as it travels from the antenna to test subject 20. For example, the actual power received $P_r$ by test subject 20 may be determined by using a variant of the well-known Friis Equation:

$$P_r = P_t G_t G_r (\lambda/4\pi R)^2,$$

where $P_r$ is the power received by test subject 20, $P_t$ is the power transmitted by the signal generator, $G_t$ is the antenna gain, $G_r$ is the gain of test subject 20 (assumed to have no gain, i.e. equal to 1), λ is the wavelength of the electromagnetic energy transmitted, and R is the distance between the antenna and test subject 20. Scanning module 100 communicates operational data, such as gain $G_t$, power transmitted $P_t$, and wavelength λ, to processing module 300. Scanning module's 100 proximity detector determines the distance R and communicates it to processing module 300. Thus, by receiving operational data from scanning module 100 regarding the gain G, power output $P_t$, wavelength λ, and distance R, processing module 300 can determine the actual power received $P_r$ by test subject 20. By calculating the difference between the power delivered EIRP to test subject 20 and the actual power received $P_r$ by test subject 20, the energy loss along the length of the RF path (i.e. path loss) may be determined.

In accordance with another aspect, processing module 300 may perform calculations to approximate certain electromagnetic properties of the biomaterials based on various test subject 20 parameters measured and calculated by processing module 300. Thus, processing module 300 may calculate electromagnetic properties of different biomaterials so that the biomaterials may be differentiated and identified.

For example, the index of refraction (n) of a biomaterial may be calculated using the well-known Frenel Equations:

$$T_n = 1 - R_n, \text{ and}$$

$$R_n = R_s = R_p = ((n_1 - n_2)/(n_1 + n_2))^2,$$

where $T_n$, is the incident power, $R_n$ ($R_s$ or $R_p$) is the reflected power, and n is the index of refraction of the biomaterial. The subscripted symbols refer to either the transverse or parallel components of the Transmitted Power, $T_n$, and the reflected Power, $R_n$. The index of refraction, n, is an electromagnetic property of all materials, even biomaterials. The incident power or transmitted power $T_n$ may also be referred to as the incident power $P_i$.

Further, based on measured and calculated parameters of test subject 20 (such as attenuation α of electromagnetic radiation, absorption/reflection of electromagnetic radiation, depth of penetration electromagnetic radiation, and emission of IR electromagnetic radiation, various electromagnetic properties of the biomaterials in test subject 20 may be calculated, such as relative static permittivity (ε), magnetic permeability (μ), and thermal energy created.

Also, various thermal properties of the biomaterials in test subject 20 may be calculated using measured change in temperature. For example, the thermal conductivity (κ) of a biomaterial may be calculated by solving the equation:

$$T_f = T_i + Q/\kappa$$

where $T_f$ is the final temperature of the biomaterial, $T_i$ is the initial temperature of the biomaterial, and Q is the amount of energy added to the biomaterial (or the transmitted power $T_n$ as described above). The initial temperature $T_i$ and the final temperature $T_f$ may be measured by detection module 200. The amount of energy added (Q) to the biomaterial may be calculated by processing module 300 based on measurements from scanning module 100 as explained above.

Once the electromagnetic properties of the biomaterials are determined, the biomaterials may be differentiated and/or identified by data module 500 to detect any anomalies.

Control Module

In one embodiment, control module 400 is connected to at least scanning module 100, detection module 200, and processing module 300. Preferably, control module 400 is connected to other modules via USB, BioBus, or other communication protocol that allows communication of signals/data among the modules. Control module 400 is adapted to control the timing, power level, antenna gain, and scan frequency of the signal generator of scanning module 100. The generator's frequency is preferably variable within the 2.450 GHz, 5.8 GHz and 24.125 GHz bands, considered to be in the radio-frequency range. Further, control module 400 is adapted to control the detection wavelengths of detection module 200. Preferably, detection module 200 operates in a wavelength range of 1 μm to 200 μm wavelengths, which are considered Near IR (NIR) to Far IR (FIR).

One of the primary functions of control module 400 is to ensure that operation of scanning module 100 is within the applicable MPE limits set forth by FCC guidelines. Additionally, control module 400 is preferably adapted to adjust the power density (S) and frequency of the electromagnetic energy delivered in order to maximize the depth of penetration and ensure proper scanning of test subject 20. In order to optimize scanning of test subject 20 while still complying with FCC MPE limits, control module 400 is arranged in a control feedback loop that allows it to monitor and adjust operation of scanning module 100.

As shown in FIG. 1, control module 400 is connected to scanning module 100. Thus, control module 400 controls the gain of the antenna and the power output of the signal generator to produce a power density (S) within the applicable FCC limit. Further, control module 400 is connected to scanning module 100 via processing module 300. Processing module 300 may perform calculations to determine whether system 10 is operating within the applicable FCC's MPE limits for power density. For example, by receiving operational data from scanning module 100 regarding the gain, output power, and distance to test subject 20, processing module 300 may calculate the power density of the electromagnetic energy delivered to test subject 20 and may send a corresponding signal to control module 400. Thus, control module 400 is adapted to compare the signal output corresponding to the power density (S) of system 10 to a reference value corresponding to the FCC MPE limit for power density and adjust operation of scanning module 100 accordingly. It should be pointed out that should the applicable FCC guidelines regarding the MPE limits be updated or replaced, control module 400 may be reprogrammed to ensure compliance.

Additionally, control module 400 is connected to detection module 200 via processing module 300. Processing module 300 may calculate the depth of penetration of the electromagnetic energy delivered to test subject 20 based on test subject 20 parameters measured by detection module 200. Thus, control module 400 may communicate with processing module 300 to determine whether the power output, antenna gain, and/or frequency of scanning module 100 may be adjusted to increase the depth of penetration of the electromagnetic energy delivered to test subject 20 while still complying with the applicable FCC MPE limits.

Imaging Module

In one embodiment, imaging module 600 may be connected to detection module 200 and data module 500. Preferably, imaging module 600 is connected to other modules via USB, BioBus, or other communication protocol that allows communication of signals/data among the modules. Imaging module 600 is preferably adapted to process, condition, and format data collected by detection module 200 and communicates this data to data module 500 to make a thermal image of test subject 20 available to both a local operator through display module 700 and to a remote operator through communications module 800. Preferably, imaging module 600 is adapted produce a real-time image on a graphical user interfaces (GUI) that employ image processing and image enhancement features which will allow for the differentiation of biomaterials based on their ability to absorb radio-frequency electromagnetic radiation and emit infrared electromagnetic radiation.

Data Module

In one embodiment, data module 500 may be connected to processing module 300, imaging module 600, display module 700, and communication module 800. Data module 500 processes data from processing module 300 and imaging module 600 and structures the data into video format for representation in display module 700 and also prepares the data for wireless transmission via communication module 800. Preferably, data module 500 is connected to other modules via protocols such as specified by the IEEE and other standards organizations that allows communication of signals/data among the modules.

In accordance with one aspect of data module 500, data module 500 receives IR radiation emission data corresponding to different locations on test subject 20 in response to irradiation at a given frequency and compares the data to known measurements of IR radiation emission for various biomaterials in response to irradiation at the same frequency. Data regarding how much IR radiation different biomaterials emit after being irradiated with RF radiation of a particular frequency or wavelength may be stored and accessed in one or more lookup tables in data module 500. Thus, data module 500 may identify and/or differentiate biomaterials based on the frequency/wavelength of the IR radiation emitted in response to irradiation with RF radiation of a given frequency. Additionally, data module 500 may receive data regarding electromagnetic properties of biomaterials in different locations in test subject 20 from processing module 300. Data regarding various electromagnetic properties of different biomaterials may be stored and accessed in one or more lookup tables in data module 500 so that data module 500 may identify and/or differentiate different biomaterials in test subject 20. Based on the data received from imaging module 600 and processing module 300, data module 500 may differentiate and/or identify the biomaterials comprising test subject 20 by providing a graphical representation of the different biomaterials via display module 700. Particularly, data module 500 may differentiate diseased or precursor tissue from normal tissue, and thus allow detection of anomalies.

Communication Module

In one embodiment, communication module 800 is connected to data module 500 and is preferably configured to have wireless access to both local and wide-area networks (LAN's and WAN's) using communication protocols such as specified by the IEEE and other standards organizations. Communication module 800 is adapted to allow sharing of diagnostic information with medical professionals and accessing of information on standard medical databases or other similar applications. Preferably, communication module 800 is connected to other modules via USB, BioBus, or other communication protocol that allows communication of signals/data among the modules.

Methods

In accordance with another aspect of the invention, provided are methods for multispectral scanning and detection of biomaterials in a test subject 20. FIG. 2 shows a flowchart of one exemplary implementation of a method 1000 in accordance with the present invention. It will be apparent to those skilled the art that the steps shown in FIG. 2 may be performed in a different order. Further, the steps show in FIG. 2 may be performed simultaneously, sequentially or separately. Still further, some of the steps shown in FIG. 2 may be omitted and/or additional steps (not shown) may be included.

In one implementation, method 1000 begins with step 1100 by irradiating a test subject 20 with RF electromagnetic radiation. More particularly, step 1100 may comprise irradiating test subject 20 with electromagnetic radiation preferably within the 2.450 GHz, 5.8 GHz and 24.125 GHz bands. Test subject 20 may be irradiated with RF electromagnetic energy, for example, by operation of scanning module 100 as described above with reference to FIG. 1.

In another implementation, method 1000 may further comprise a step 1200 of detecting IR electromagnetic radiation emitted by test subject 20 as it absorbs RF electromagnetic energy and converts it into thermal energy. Step 1200 may be performed, for example, by operation of detection module 200 as described above with reference to FIG. 1.

In another implementation, method 1000 may further comprise a step 1300 of measuring and/or calculating parameters of the RF electromagnetic radiation impinged on test subject 20. In particular, step 1300 may comprise performing calculations to determine different aspects of the system's 10 performance, such as EIRP, power density, path loss, power incident, and power reflected. Further, step 1300 may comprise performing calculations to determine whether the electromagnetic radiation complies with applicable FCC MPE limits for power density. Step 1300 may be performed, for example, by operation of scanning module 100 and processing module 300 as described above with reference to FIG. 1.

In another implementation, method 1000 may further comprise a step 1400 of measuring and/or calculating parameters of test subject 20 during irradiation. In particular step 1400 may comprise measuring and/or calculating electromagnetic energy absorbed by test subject 20, electromagnetic energy reflected by test subject 20, depth of penetration of electromagnetic energy into test subject 20, initial temperature of test subject 20, and final temperature of test subject 20. Step 1400 may be performed, for example, by operation of detection module 200 and processing module 300 as described above with reference to FIG. 1.

In another implementation, method 1000 may further comprise a step 1500 of adjusting irradiation of test subject 20 based on measured and/or calculated parameters of the RF electromagnetic radiation and test subject 20 to control the electromagnetic radiation output to comply with applicable FCC MPE limits while maximizing the depth of penetration to ensure proper scanning of test subject 20 as described above. In particular, step 1500 may comprise adjusting the output power, antenna gain, and frequency of a signal generator to obtain maximum penetration of test subject 20 while complying with applicable FCC MPE limits. Step 1500 may be performed, for example, by operation of processing module 300, control module 400, and scanning module 100 as described above with reference to FIG. 1.

In another implementation, method 1000 may further comprise a step 1600 of calculating electromagnetic properties of biomaterials in test subject 20 based on measured and/or calculated parameters of test subject 20 during irradiation. More particularly, step 1600 may comprise calculating electromagnetic properties of the biomaterials in test subject 20, such as relative static permittivity ($\epsilon$), magnetic permeability ($\mu$), and thermal energy based on measured and calculated parameters of test subject 20, such as attenuation $\alpha$ of electromagnetic radiation, absorption/reflection of electromagnetic radiation, depth of penetration electromagnetic radiation, emission of IR electromagnetic radiation, and change in temperature. Step 1600 may be performed, for example, by operation of processing module 300 and detection module 200 as described above with reference to FIG. 1.

In another implementation, method 1000 may further comprise a step 1700 of differentiating and/or identifying biomaterials in test subject 20 based on IR electromagnetic radiation emitted by different biomaterials and/or the calculated electromagnetic properties of different biomaterials. Step 1700 may be performed, for example, by operation of detection module 200, processing module 300, and data module 500 as described above with reference to FIG. 1.

In another implementation, method 1000 may comprise a step 1800 of providing an image of a scanned portion of test subject 20 differentiating and/or identifying different biomaterials. Step 1800 may be performed, for example, by operation of data module 500, imaging module 600, and display module 700 as described above with reference to FIG. 1.

In another implementation, method 1000 may comprise a step 1900 of transmitting data to a medical practitioner and/or accessing data from a medical database for the purpose of diagnosing test subject 20. Step 1900 may be performed, for example, by operation of communication module 800 via a wireless air interface communication protocols such as specified by the IEEE and other standards organizations.

What is claimed:

1. A method for scanning and detecting biomaterials within a test subject for medical diagnosis, which comprises:
   irradiating a portion of the test subject by applying at a distance from the subject RF electromagnetic radiation having a frequency in the range of 2.4-2.5 GHz, 5.725-5.875 GHz or 24-24.25 GHz, and at a density that is between 1 and 100 mW/cm$^2$ with the radiation applied to maximize depth of penetration to ensure proper scanning of the biomaterials and at a time weighted average power density that is below an exposure of 5 mW/cm$^2$ for 6 minutes so as to not harm or injure the subject;
   measuring parameters of the irradiation incident on the test subject;
   detecting IR electromagnetic radiation data emitted by said portion of irradiated biomaterials of the test subject; and
   presenting a thermal image of said portion of the test subject differentiating different levels of IR electromagnetic radiation emitted.

2. The method of claim 1 which further comprises adjusting the irradiation of the test subject based on the measured parameters of the irradiation.

3. The method of claim 2 which further comprises measuring parameters of the test subject during irradiation.

4. The method of claim 2 which further comprises determining electromagnetic properties of different biomaterials in the test subject based on the measured parameters of the test subject.

5. The method of claim 2 which further comprises differentiating biomaterials in the test subject based on the electromagnetic properties of different biomaterials.

6. The method of claim 2 which further comprises transmitting or accessing data for diagnosing the test subject.

7. A system for scanning and detecting biomaterials in a test subject for medical diagnosis, comprising:
   a scanning module adapted to irradiate the test subject with RF electromagnetic radiation having a frequency in the range of 2.4-2.5 GHz, 5.725-5.875 GHz or 24-24.25 GHz, and at a density that is between 1 and 100 mW/cm$^2$ with the radiation applied to maximize depth of penetration to ensure proper scanning of the biomaterials and at a time weighted average power density that is below an exposure of 5 mW/cm$^2$ for 6 minutes so as to not harm or injure the subject;
   a detection module adapted to measure test subject parameters including IR electromagnetic radiation emitted by the irradiated biomaterials of the test subject; and
   an imaging module adapted to produce an image of the detected test subject parameters.

8. The system of claim 7 further comprising a processing module for determining electromagnetic properties of biomaterials in the test subject based on measured test subject parameters.

9. The system of claim 7 wherein the scanning module provides irradiation to the test subject that remains within acceptable limits.

10. The system of claim 7 further comprising a communication module that accesses data from local or remote locations.

11. The system of claim 7 further comprising a display for displaying an image produced by the imaging module.

12. The method of claim 1 wherein the irradiation is non-ionizing electromagnetic radiation having one of the recited frequencies.

13. The method of claim 2 wherein the measuring of the parameters of the irradiation incident on the test subject includes performing calculations to determine system performance relating to incident RF electromagnetic radiation, effective isotropic irradiated power, power density, path loss, incident power, and reflected power.

14. The method of claim 2 wherein the RF electromagnetic radiation is adjusted to obtain a maximized depth of penetration to ensure proper scanning of the test subject.

15. The method of claim 2 wherein the differentiating of the biomaterials is based on measuring or calculating attenuation electromagnetic radiation, absorption or reflection of electromagnetic radiation, depth of electromagnetic radiation penetration, emission of RF electromagnetic radiation, or created thermal energy.

16. The system of claim 7 wherein the scanning module includes a signal generator that has a variable power output of 1 mW to 1000 mW and a duty cycle of 100% or less and which produces non-ionization electromagnetic radiation having the recited frequency.

17. The system of claim 16 further comprising a control module electronically connected at least to the scanning module to adjust the RF electromagnetic radiation.

18. The system of claim 16 wherein the RF electromagnetic radiation is adjusted by control of the timing, power level, antenna gain, or scan frequency of the signal generator of scanning module.

19. The system of claim 16 wherein the control module is also connected to the detection module via the processing module, to provide a communication protocol that allows communication of signals or data among the modules.

20. The system of claim 16 wherein the processing module calculates depth of penetration of the RF electromagnetic radiation delivered to test subject based on parameters measured by detection module, and the control module communicates with the processing module to determine whether to adjust the power output, antenna gain, or frequency of scanning module to increase the depth of penetration of the RF electromagnetic radiation delivered to test subject.

* * * * *